United States Patent
Murphy

(10) Patent No.: US 7,830,161 B2
(45) Date of Patent: Nov. 9, 2010

(54) METHODS FOR MEASUREMENT OF FLUID ELECTRICAL STABILITY

(75) Inventor: Robert Murphy, Kingwood, TX (US)

(73) Assignee: Halliburton Energy Services Inc., Duncan, OK (US)

(*) Notice: Subject to any disclaimer, the term of this patent is extended or adjusted under 35 U.S.C. 154(b) by 347 days.

(21) Appl. No.: 12/192,763

(22) Filed: Aug. 15, 2008

(65) Prior Publication Data

US 2010/0042335 A1 Feb. 18, 2010

(51) Int. Cl.
G01R 27/08 (2006.01)
G01R 27/22 (2006.01)
G01V 3/00 (2006.01)

(52) U.S. Cl. .................. 324/698; 324/92; 324/366

(58) Field of Classification Search .............. 324/92, 324/366, 698
See application file for complete search history.

(56) References Cited

U.S. PATENT DOCUMENTS

| | | | |
|---|---|---|---|
| 2,859,404 | A | 5/1955 | Crittendon |
| 4,008,922 | A | 2/1977 | Kallin et al. |
| 4,134,799 | A | 1/1979 | Allen et al. |
| 4,315,421 | A | 2/1982 | Wilson |
| 4,481,121 | A | 11/1984 | Barthel |
| 4,663,076 | A | 5/1987 | Clapper et al. |
| 4,728,404 | A * | 3/1988 | Renzler ............... 205/744 |
| 5,345,819 | A | 9/1994 | Dearing |
| 5,811,841 | A | 9/1998 | Ganguly et al. |
| 6,006,831 | A | 12/1999 | Schlemmer et al. |
| 6,154,710 | A | 11/2000 | Kobayashi et al. |
| 6,335,100 | B1 | 1/2002 | Tominaga et al. |
| 6,509,738 | B1 | 1/2003 | Minerbo et al. |
| 6,525,003 | B2 | 2/2003 | Schlemmer et al. |
| 6,906,535 | B2 | 6/2005 | Murphy et al. |
| 7,373,276 | B2 * | 5/2008 | Beetge ............... 702/182 |
| 2003/0206024 | A1 | 11/2003 | Murphy, Jr. et al. |
| 2006/0129341 | A1 * | 6/2006 | Beetge ............... 702/65 |

FOREIGN PATENT DOCUMENTS

WO 2006/065912 A1 6/2006

OTHER PUBLICATIONS

U.S. Appl. No. 11/872,087, filed Oct. 15, 2007, entitled "Methods and Systems for Measurement of Fluid Electrical Stability," by Murphy.
International Search Report filed Aug. 6, 2009, re International Application No. PCT/GB2009/001937.
American Petroleum Institute, "Recommended Practice Standard Procedure for Field Testing Oil-Based Drilling Fluids," Third Edition, Feb. 1998.
Growcock, F.B., "Electrical Stability, Emulsion Stability, and Wettability of Invert Oil-Based Muds," SPE Drilling & Completion, Mar. 1994.

* cited by examiner

Primary Examiner—Timothy J Dole
(74) Attorney, Agent, or Firm—John W. Wustenberg; Baker Botts L.L.P.

(57) ABSTRACT

The invention relates particularly to methods and apparatuses for characterizing water-in-oil or invert emulsion fluids for use in drilling well bores in hydro-carbon bearing subterranean formations. A fluid stability measurement method is described. The method includes placing a sample of an emulsion in a gap between electrodes, disturbing the sample, measuring the electrical stability of the sample, and establishing a relationship between electrical stability and time since the sample was disturbed.

23 Claims, 4 Drawing Sheets

METHODS FOR MEASUREMENT OF FLUID ELECTRICAL STABILITY

BACKGROUND OF THE INVENTION

The present invention relates to methods and apparatuses for characterizing or evaluating the strength or effectiveness of oil-based drilling fluids for use in drilling well bores in subterranean formations. The invention relates particularly to methods and apparatuses for characterizing water-in-oil or invert emulsion fluids for use in drilling well bores in hydrocarbon bearing subterranean formations.

Drilling fluids are frequently used in oil and gas drilling operations. These fluids serve many purposes including, but not limited to, removing the cuttings produced, lubricating and cooling the drill bit, and supporting the walls of the hole being drilled. Oil-based drilling fluids are frequently used when drilling wells for oil and gas. These oil-based drilling fluids are typically water-in-oil emulsions that are stabilized with the addition of emulsifiers. The water phase is usually about 5% to about 40% of the total liquid volume and is usually comprised of (but not limited to) calcium chloride brine. If the formulation of the invert emulsion drilling fluid becomes unbalanced, due to, for example (without limitation), contamination, improper product additions, or thermal degradation, the oil-based drilling fluids tend to revert to an oil-in-water emulsion. As a result of the reversion to an oil-in-water emulsion, the water becomes the continuous phase and can cause the solids in the drilling fluid to become water wet. Such wetting has significant negative consequences to a drilling operation and requires expensive remedial action in order to prevent the loss of the well.

Electrical Stability measurements give an indication of the stability of a water-in-oil emulsion. In order to characterize the stability of a water-in-oil emulsion, a strong electric field is applied across a small gap between two electrodes. Normally, alternating current (AC) electrical fields are applied to mitigate damage to the surfaces of the electrodes. The gap is filled with a sample of the fluid to be tested. The electric field is increased until significant current flows through the sample between the electrodes. Oil based drilling fluids with emulsified brine are essentially electrical insulators to weak electric fields. As the field strength increases, the emulsified droplets of water in the electrode gap begin to elongate and align with the electric field. If the electric field is sufficiently strong, the droplets may eventually merge, forming a conductive bridge across the electrode gap. The droplet bridge can conduct a significant electric current. The moment that the current exceeds a specified trip current is described as breakdown.

It has been demonstrated that the field strength at breakdown, measured in peak volts across the electrode gap, is related to the stability of the emulsion. (Growcock F B, Ellis C F and Schmidt D D: "Electrical Stability, Emulsion Stability, and Wettability of Invert Oil-Based Muds," SPE Drilling & Completion 9, no. 1 (March 1994): 39-46.) The peak voltage required to cause the breakdown is defined as Electrical Stability of the oil-based drilling fluid. The higher the peak voltage at which this breakdown occurs, the greater is the Electrical Stability of the fluid being tested. The American Petroleum Institute's "Recommended Practice Standard Procedure for Field Testing Oil-Based Drilling Fluids", API Recommended Practice 13B-2, Third Edition, February 1998 ("the API Procedure"), is incorporated herein by reference. Paragraph 8.1.1 of the API Procedure defines the Electrical Stability of an oil-based drilling fluid as "the voltage in peak volts-measured when the current reaches 61 µA."

The Electrical Stability measurement is affected by the electrode configuration, AC frequency, gap width, trip current, and the rate of increase of the electrical field. All of these parameters have been specified in the procedures of the American Petroleum Institute (API) for use in the industry. The API Procedure requires that before an Electrical Stability measurement, the sample fluid should be stirred for 10 seconds.

However, the Electrical Stability, as measured by current manual methods, is known to be sensitive to operator methodology and many components of the drilling fluid. Additionally, typical methods of measuring Electrical Stability of oil-based drilling fluids do not account for the effects of fluid gelation over time. Such pitfalls make current methods of measuring Electrical Stability prone to errors and, therefore, less useful.

Such problems are further compounded by how time-consuming current methods are. The typical methods yield very few data points to distinguish trends. Additionally, traditional Electrical Stability measurements are relatively noisy due to the non-homogeneous nature of drilling fluids.

SUMMARY OF THE INVENTION

The present invention relates to methods and apparatuses for characterizing or evaluating the strength or effectiveness of oil-based drilling fluids for use in drilling well bores in subterranean formations. The invention relates particularly to methods and apparatuses for characterizing water-in-oil or invert emulsion fluids for use in drilling well bores in hydrocarbon bearing subterranean formations.

In one embodiment, the present invention is directed to a method of determining electrical stability of an emulsion. A sample of the emulsion is placed in a gap between a first electrode and a second electrode. A vane is passed through at least a portion of the sample, and completion of the passing is associated with a dwell start time. A potential difference between the first electrode and the second electrode is increased so that a current flow therebetween reaches a threshold value, wherein the increasing begins at a voltage increase start time. The current flow is monitored. A dwell interval is determined, and the dwell interval depends on the dwell start time and a time when the current flow reaches the threshold value. One or more measurements of potential difference are taken and recorded.

In another embodiment, the present invention is directed to a method of determining electrical stability of an emulsion where at least a portion of a sample of the emulsion is disturbed, and completion of the disturbing is associated with a first dwell start time. A first potential difference across the sample is increased at least until a first current flow through the sample reaches a threshold value. A first potential difference value corresponding to the threshold value is determined. A first dwell interval is determined, and the first dwell interval is based at least in part on the first dwell start time and a time when the first current flow reaches the threshold value.

In yet another embodiment, the present invention is directed to a computer program, stored in a tangible medium for determining electrical stability of an emulsion. The computer program includes executable instructions to cause at least one processor to initiate a process for disturbing at least a portion of a sample of the emulsion, where completion of the disturbing is associated with a first dwell start time. The process includes increasing a first potential difference across the sample at least until a first current flow through the sample reaches a threshold value. The process also includes determining a first potential difference value corresponding to the first threshold value. The process further includes determining a first dwell interval, where the first dwell interval is an amount of time based at least in part on the first dwell start time and a time when the current flow reaches the threshold value.

The features and advantages of the present invention will be apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

DESCRIPTION OF PREFERRED EMBODIMENTS

The present invention relates to methods and apparatuses for characterizing or evaluating the strength or effectiveness of oil-based drilling fluids for use in drilling well bores in subterranean formations. The invention relates particularly to methods and apparatuses for characterizing water-in-oil or invert emulsion fluids for use in drilling well bores in hydrocarbon bearing subterranean formations.

Drilling fluids are usually formulated so that they have gel strength when they are static. Gel strength represents the shear stress required to start the fluid moving after a quiescent period. Drilling fluids gel when not agitated, becoming somewhat solid or plastic. This aids in the suspension of particulate material in the drilling fluid. The gel is easily broken by mixing, shearing or otherwise sufficiently disturbing the fluid. By industry standard, gel strength is normally measured by obtaining the peak dial reading of a specified geometry rheometer at 3 rpm after being static for 10 seconds, 10 minutes and 30 minutes. The gel strength typically increases from less than 7 lb/100 ft$^2$ immediately after shearing, to values of as much as 30 lb/100 ft$^2$ within 30 minutes. Gel strength and the rate at which it forms are very important properties of drilling fluids that are taken into account in methods of the present invention.

Figure 1:
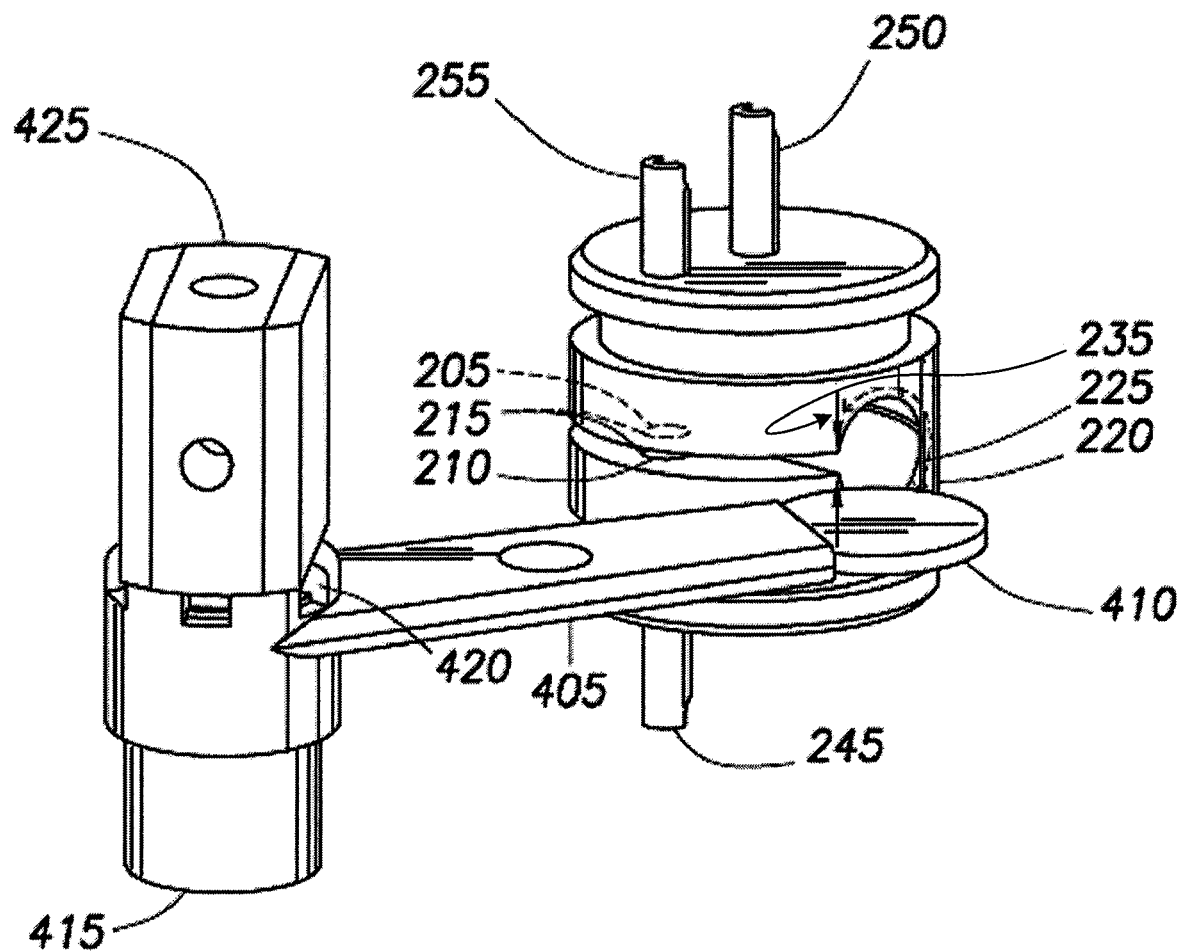
FIG. 1 is a perspective view of a Self Cleaning Electrical Stability Tester Cell.

The API Procedure requires that, before an Electrical Stability measurement is taken, the sample fluid should be stirred for 10 seconds. The stirring of the API Procedure is mimicked by the methods and apparatuses described in application Ser. No. 11/872,087 entitled, "Methods and Systems for Measurement of Fluid Electrical Stability," which is incorporated by reference in its entirety herein for all purposes. FIG. 1 shows an example of one embodiment of an apparatus of that application. In that example, cleaning vane 410 is near electrode gap 235 between first and second electrodes 205 and 210. Vane 410 rotates about pivot 415 on arm 405 to pass into electrode gap 235. Additional elements, examples and modifications are described in application Ser. No. 11/872,087.

Shearing the fluid in the gap between the electrodes of the electrode assembly may accomplish several things: 1) it may destroy any conductive trail through the sample between the electrodes that may have remained after a previous Electrical Stability measurement; 2) it may mix the fluid and makes it more homogeneous; and 3) it may break down any gel structure that may have formed. In the example of FIG. 1, vane 410 may be cycled into gap 235 and back out 10 times, for example, before a measurement. However, any number of cycles that would sufficiently shear the fluid and shear off solids on the electrode face could be used. Because the cleaning vane of such an apparatus is passed through the electrode gap just before a measurement, the moment when the vane stops the shear can be accurately determined. A gel may begin to form at the time the vane passes out of the electrode gap. This may allow an accurate determination of the elapsed time from the moment of shear cessation to the breakdown event (i.e., when current begins to pass through the fluid) to establish the Electrical Stability measurement.

Figure 2:
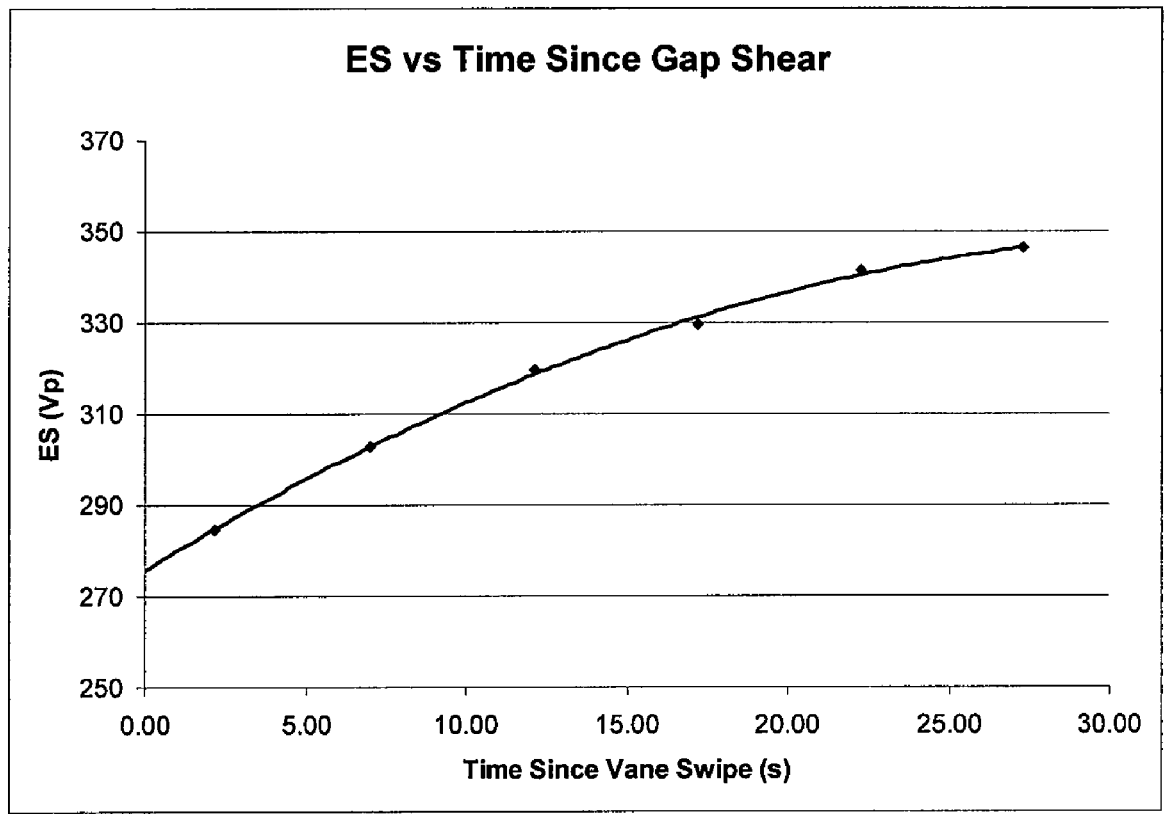
FIG. 2 is illustrates an example showing a variation of Electrical Stability with a delay between shear cessation and a time of Electrical Stability measurement.

Testing with a prototype apparatus according to one embodiment of application Ser. No. 11/872,087 and a sample of drilling fluid shows that the Electrical Stability measurement is dependent on the elapsed time from shear cessation to the current breakdown event. To facilitate a better understanding of the present invention, the example of FIG. 2 illustrates variation of Electrical Stability with the delay between shear cessation and the time of Electrical Stability measurement. In no way should the example be read to limit, or define, the scope of the invention. To smooth the representation of the data, each data point may represent the average of multiple measurements.

It is thought that the increase in Electrical Stability with dwell time, as illustrated in FIG. 2, is due to the structure of the gel forming, strengthening, and inhibiting droplets of the water phase of the emulsion from merging and bridging the gap between the electrodes to form a conductive path. The increase in Electrical Stability with time likely is proportional to the increase in gel strength with time. Since gel strength stops increasing after about 30 minutes for most drilling fluids, the Electrical Stability likely will also stop increasing. Accordingly, coordinated multiple measurements of the Electrical Stability could be used to obtain an indirect measurement of the strength and formation rate of drilling fluid gels.

To minimize the effect variations in gel properties have on Electrical Stability measurements, the time from shear cessation to the moment of electrical breakdown should be kept constant. This is not practical with the traditional instruments for measuring the Electrical Stability, such as Fann Instrument Company's Model 23D Electrical Stability Tester (EST). However, with suitable control software, the apparatuses described in application Ser. No. 11/872,087 can make the measurements required.

Figure 3:
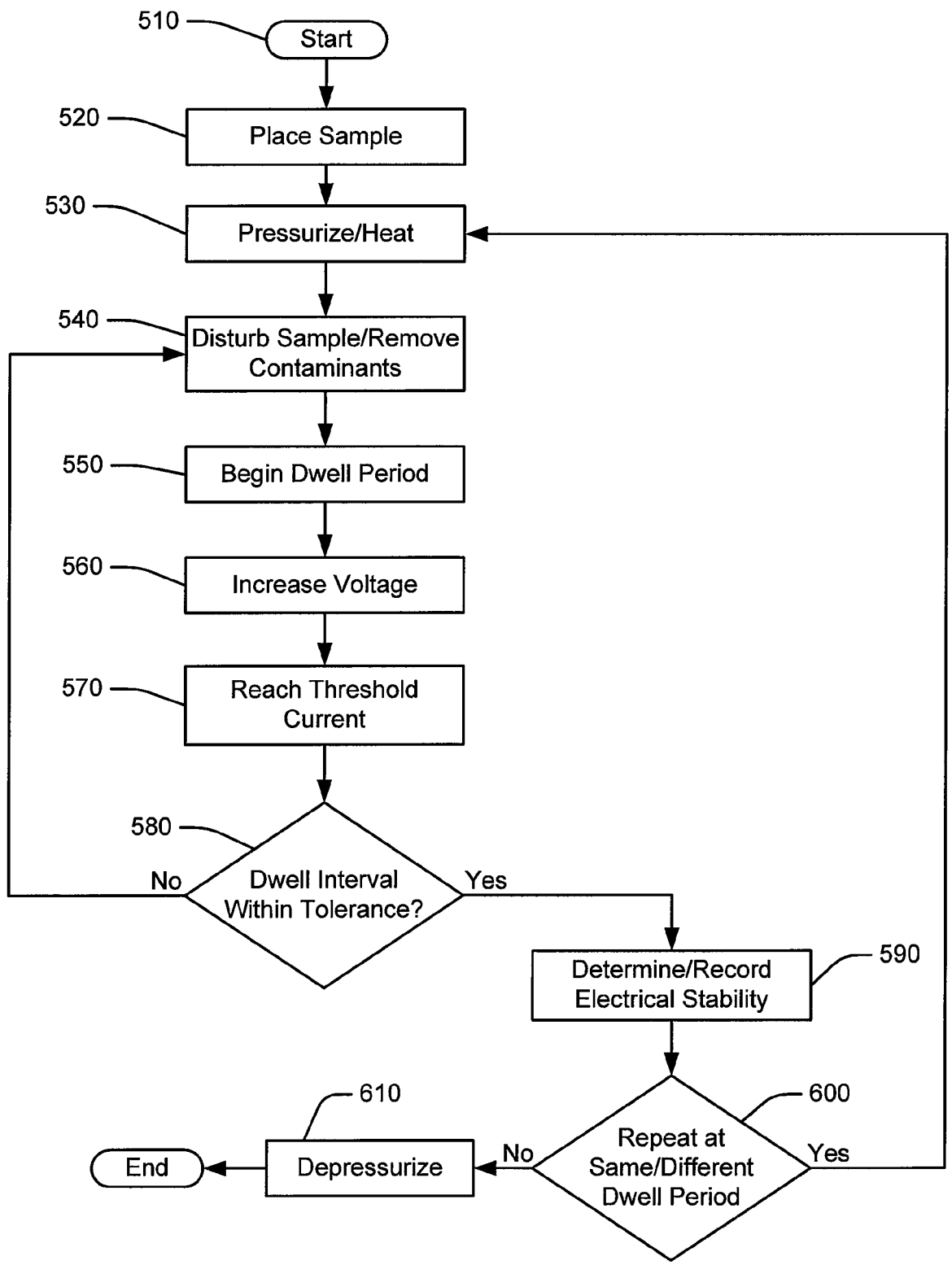
FIG. 3 generally illustrates one example flowchart of one implementation of a method of the present invention.

An example of one implementation of a method of the present invention is illustrated generally in FIG. 3. Method 500 begins generally at step 510. At step 520, a fresh sample of fluid, such as an emulsion, may be circulated into the measurement space, which may contain the electrodes of the Electrical Stability measurement circuit. At step 530, the sample may be pressurized to minimize the effects of entrained air bubbles. The sample also may be heated to a test temperature.

At step 540, the sample may be disturbed to mix the sample and break gels. This can be accomplished in the example embodiment of FIG. 1 by passing vane 410 through electrode gap 235. As described in an example above, cleaning vane 410 can be cycled through electrode gap 235 a number of times, though certain embodiments of the present invention do not require multiple passings. The passing of vane 410 also can act to remove contaminates from the electrodes. As will be appreciated by those of ordinary skill in the art, other approaches could be used to shear or sufficiently disturb the fluid in electrode gap 235. The physical geometry of cleaning vane 410, illustrated as a disk, could take many forms. For example, it could be a cylindrical rod or a brush that mixes the fluid and physically abrades the surfaces of electrode gap 235. Other alternatives to vane-like elements could be used. For example, a jet of the sample that ended relatively abruptly could accomplish the same end.

At step 550, the dwell interval starts when, for example, cleaning vane 410 passes out of electrode gap 235 for the last time. More generally, where alternatives to a vane are used, the dwell interval starts at a dwell start time when the mechanical disturbing of the fluid ends.

At step 560, the potential difference between the electrodes is increased for the Electrical Stability measurement. The time at which the potential difference begins to increase is the voltage increase start time. The current flow may be monitored throughout this process. In certain embodiments, the start voltage between the electrodes may be 0 volts; in other embodiments, other start voltages could be used. The voltage increase could be in the form of a voltage ramp. The API Procedure specifies 150 V/s, but other ramp rates or rates of increase could be used. The API Procedure also specifies a 340 Hz sine wave of low distortion. As will be appreciated by those of ordinary skill, other frequencies, waveforms or manners of increase may be more useful for the purposes of these methods. DC voltage could also be used, and, to minimize electrode damage, the polarity could be reversed each time a measurement is made.

In the case of fluids with high Electrical Stability values, it may be necessary to start the voltage ramp immediately after shear cessation and/or at a voltage higher than zero. This could allow the drive circuit to reach the Electrical Stability voltage within a specified dwell interval while retaining a desired ramp rate.

At step 570, the voltage across electrode gap 235 may increase at least until current flow that passes between the electrodes reaches the API specified trip current of 61 microamperes. For the purposes of this invention, threshold values other than 61 microamperes could be specified.

At step 580, the elapsed time or dwell interval from the end of cleaning vane shear (dwell start time) to the moment of current breakdown (when the current flow reaches the threshold value) may be calculated. If the dwell interval is not within a specified dwell interval range (e.g., 10±1 s), the process may be repeated starting at step 540. For the repetition, the time interval between the start of a dwell interval and the start of the voltage ramp may be changed to bring the actual dwell interval inside of the specified tolerance. In this way, the time between shear cessation and the Electrical Stability measurement will be closely controlled.

At step 590, if the dwell interval is within the specified tolerance of the dwell interval, the Electrical Stability value in volts peak, which corresponds to the point of current breakdown, may be recorded. In addition to the Electrical Stability value, it may be desirable to also calculate the break energy as detailed in U.S. Pat. No. 6,906,535.

At step 600, if no further measurements need to be taken, the sample may be depressurized at step 610 for the interim until a subsequent measurement process is begun. However, at step 600, the process may be repeated beginning again at step 530, for example, as needed to record additional Electrical Stability values at a particular dwell interval. The process also may be repeated beginning again at step 530, for example, to record additional Electrical Stability values at a second dwell interval. For example, cleaning vane 410 is passed through at least a portion of the sample again, and completion of that passing is associated with a second dwell start time. A second potential difference is increased across the fluid sample at least until a current flow reaches the threshold value. A second dwell interval is determined based on the second dwell start time and a second time when current flow reaches the threshold value. A second Electrical Stability value in volts peak corresponding to the current breakdown point may be recorded. The use of the term "second" herein is only intended for clarity of description and is not intended as a limitation. For example, the "second potential difference" need not directly follow a "first potential difference" and need not be have a voltage different from a "first potential difference"—both could start at 0 volts. Thus, the process may be repeated one or more times to record Electrical Stability values at different dwell intervals to establish a relationship between Electrical Stability of the sample and time since the sample was agitated (i.e., dwell interval), such as that illustrated in the example of FIG. 2.

Since the Electrical Stability voltage measurement can be dependent on how recently the sample fluid in the measurement gap was sheared or agitated, frequent measurements must be obtained in order to monitor the strength and characteristics of the oil-based drilling fluid during the drilling operations. An advantage of measurements of Electrical Stability obtained with this method is that the time between shear cessation and the Electrical Stability measurement will be closely controlled. This time period is not specified in the API Procedure, but can significantly affect the results. In the example represented in FIG. 2, the dwell time affected the results by 21% for a dwell difference of about 25 seconds.

Figure 4:
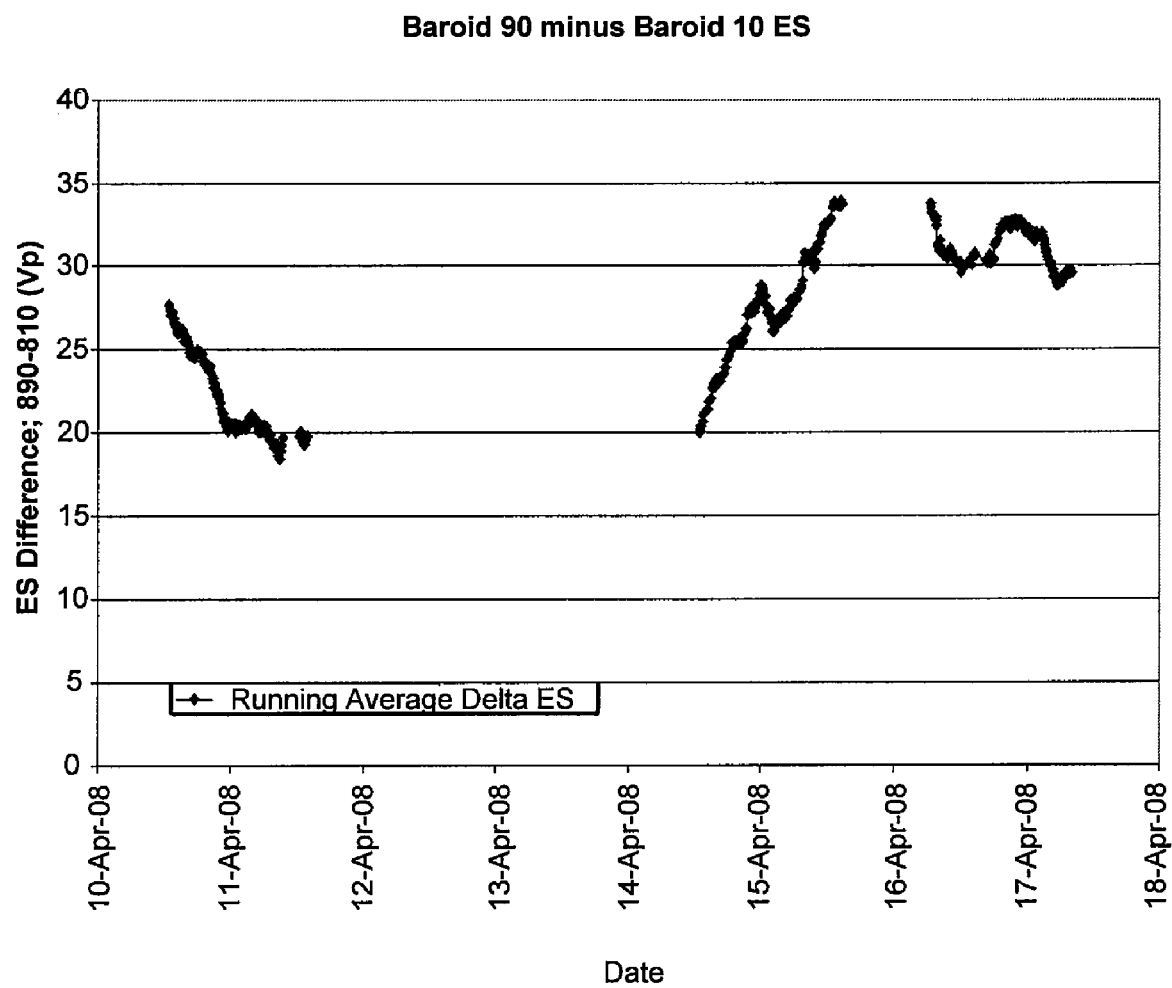
FIG. 4 illustrates an example of data showing the variability of the Electrical Stability with time.

To facilitate a better understanding of the present invention and the variability of the Electrical Stability with time, the example of FIG. 4 is provided. In no way should the example be read to limit, or define, the scope of the invention. The graph of FIG. 4 was obtained by a prototype of one embodiment of the apparatuses described in application Ser. No. 11/872,087. The graph represents the data obtained on an agitated 500-barrel sample of drilling fluid taken over a several day period. The gaps in the data correspond to periods when the instrument was shut down. To obtain this data, the apparatus was programmed to obtain Electrical Stability measurements at 3 different dwell intervals after shearing with the cleaning vane ceased: 10 seconds, 30 seconds, and 90 seconds, designated "Baroid 10", "Baroid 30" and "Baroid 90", respectively. FIG. 4 represents the running average of the difference between the "Baroid 90" and "Baroid 10" measurements.

A comparison to the local weather suggests that the variation represented in the graph of FIG. 3 is caused primarily by changes in the relative humidity of the air over the open-topped tank that held the sample. Post cold front low humidity probably removed water from the brine phase of the synthetic oil based drilling fluid. Conversely, the high humidity associated with the frontal approach and passage caused the brine phase of the drilling fluid to absorb water from the air. The data suggest, as those familiar with drilling fluids would expect, that the change in oil-water ratio had an effect on the gel properties of the fluid.

At low shear, the viscosity of a drilling fluid is partially a function a dynamic balance between the strength of gel that is trying to form and the breaking of the gel due to the stress. Low shear rheological behavior is an extremely important property of drilling fluids that must be controlled closely. This is especially true for highly deviated boreholes.

One common practice entails taking gel strength measurements at 4-hour intervals while drilling a well. The typical measurements yield very few data points to distinguish trends. However, apparatuses described in application Ser. No. 11/872,087 are capable of making measurements according to the methods taught herein at intervals of 6 minutes or less. The trend of the gel strength, and thus low shear properties, can be closely tracked with the methods taught herein.

Traditionally, Electrical Stability measurements are relatively noisy due to the non-homogeneous nature of drilling fluids, especially when the scale of the sample tested is small, such as on the order of 0.01 ml. Frequent measurements using the methods of the present invention are required to clearly discern trends. For example, unexpected trends in the Electrical Stability as a function of time from quiescence like FIG. 4 can be used to alert operators of needed corrective action during the drilling of well.

In general, the gel strength of a drilling fluid is maintained in a fairly narrow range. It is likely that some of the situations that will affect gel strength have not yet been discovered or are poorly understood due to lack of frequent gel measurements correlated with drilling rig activity events. Frequent measurements using this method will lead to better understanding and management of the properties of the drilling fluid. An automated real-time system of reporting the Electrical Stability values measured by this disclosed method would give early notice of many issues that can threaten the successful completion of a well. For example, gel strength is sensitive to many drilling fluid contaminates and additives.

While a time-dependent function of Electrical Stability after shear has been demonstrated, the time periods of the demonstrated data are merely exemplary. Dwell intervals up to 30 minutes can be justified based on experience with measuring gel strengths. However, longer dwell intervals would limit the frequency of measurements with a single apparatus.

As mentioned above, it may be desirable to also calculate the break energy as detailed in U.S. Pat. No. 6,906,535 in addition to the Electrical Stability value. Time dependent differences in Break Energy may reveal other useful trends. The Break Energy measurement can be made at the same time as the Electrical Stability measurement using this method.

As can be appreciated by one of ordinary skill in the art, one or more methods of the present invention may be implemented via an information handling system. For purposes of this disclosure, an information handling system may include any instrumentality or aggregate of instrumentalities operable to compute, classify, process, transmit, receive, retrieve, originate, switch, store, display, manifest, detect, record, reproduce, handle or utilize any form of information, intelligence or data for business, scientific, control or other purposes. For example, an information handling system may be a personal computer, a storage device, or any other suitable device and may vary in size, shape, performance, functionality and price. The information handling system may include random access memory, one or more processing resources such as a central processing unit or hardware or software control logic, ROM and/or other types of nonvolatile memory. Additional components of the information handling system may include one or more disk drives, one or more network ports for communication with external devices as well as various input and output devices, such as a keyboard, a mouse and a video display. The information handling system may also include one or more buses operable to transmit communications between the various hardware components.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A method of determining electrical stability of an emulsion, the method comprising:
   placing a sample of the emulsion in a gap between a first electrode and a second electrode;
   passing a vane through at least a portion of the sample, wherein completion of the passing indicates a dwell start time;
   increasing a potential difference between the first electrode and the second electrode until a current flow therebetween reaches a threshold value, wherein the increasing begins at a voltage increase start time;
   monitoring the current flow;
   determining a dwell interval, wherein the dwell interval is a time period between the dwell start time and a time when the current flow reaches the threshold value;
   taking one or more measurements of potential difference;
   recording the one or more measurements; and
   determining electrical stability of the emulsion if the dwell interval is within a dwell interval range.

2. The method of claim 1, comprising:
   determining if the dwell interval is not within the dwell interval range;
   passing the vane through at least a portion of the sample again;
   increasing the potential difference, wherein one or more of the voltage increase start time, a start voltage and a rate of increase are adjusted such that the dwell interval is within the dwell interval range.

3. The method of claim 1, further comprising:
   passing the vane through at least a portion of the sample again, wherein completion of the passing indicates a second dwell start time;
   increasing a second potential difference;
   determining a second dwell interval, wherein the second dwell interval is a time period between the second dwell start time and a subsequent time when a second current flow reaches the threshold value;
   taking one or more additional measurements of potential difference; and
   recording the one or more additional measurements.

4. The method of claim 3, further comprising:
   determining a relationship between electrical stability of the sample and a plurality of dwell intervals, based at least in part on the dwell interval, the second dwell interval, the one or more measurements, and the one or more additional measurements.

5. The method of claim 4, wherein:
   one or both of the potential difference and the second potential difference begins increasing from a voltage other than zero volts.

6. The method of claim 4, wherein increasing the potential difference and increasing the second potential difference further comprise increasing an AC voltage applied across the first electrode and the second electrode.

7. The method of claim 1, further comprising passing the sample through a filter before placing the sample in the gap between the first electrode and the second electrode.

8. The method of claim 1, further comprising pressurizing the sample to minimize effects of entrained air bubbles.

9. The method of claim 1, further comprising heating the sample to a test temperature.

10. A method of determining electrical stability of an emulsion, the method comprising:
- disturbing at least a portion of a sample of the emulsion, wherein completion of the disturbing indicates a first dwell start time;
- increasing a first potential difference across the sample at least until a first current flow through the sample reaches a threshold value;
- determining a first potential difference value corresponding to the threshold value;
- determining a first dwell interval, wherein the first dwell interval is a time period between the first dwell start time and a time when the first current flow reaches the threshold value; and
- determining electrical stability of the emulsion if the dwell interval is within a dwell interval range.

11. The method of claim 10, further comprising:
- again disturbing at least a portion of the sample, wherein completion of the disturbing indicates a second dwell start time;
- increasing a second potential difference across the sample at least until a second current flow reaches the threshold value;
- determining a second potential difference value corresponding to the threshold value; and
- determining a second dwell interval, wherein the second dwell interval is a time period between the second dwell start time and a time when the second current flow reaches the threshold value.

12. The method of claim 11, further comprising:
- characterizing a relationship between electrical stability of the sample and a plurality of dwell intervals, based at least in part on the first and second dwell intervals and the first and second potential difference values.

13. The method of claim 12, wherein one or both of the first potential difference and the second potential difference begin to increase from a voltage other than zero volts.

14. The method of claim 12, wherein increasing the first potential difference and increasing the second potential difference further comprise increasing an AC voltage applied across the sample.

15. The method of claim 10, further comprising pressurizing the sample to minimize the effects of entrained air bubbles.

16. The method of claim 10, further comprising heating the sample to a test temperature.

17. A computer program stored in a tangible medium for determining electrical stability of an emulsion, including executable instructions to cause at least one processor to process a routine for:
- disturbing at least a portion of a sample of the emulsion, wherein completion of the disturbing indicates a first dwell start time;
- increasing a first potential difference across the sample at least until a first current flow through the sample reaches a threshold value;
- determining a first potential difference value corresponding to the first threshold value;
- determining a first dwell interval, wherein the first dwell interval is a time period between the first dwell start time and a time when the current flow reaches the threshold value; and
- determining electrical stability of the emulsion if the dwell interval is within a dwell interval range.

18. The computer program of claim 17, where the computer program further comprises executable instructions to cause at least one processor to process a routine for:
- again disturbing at least a portion of the sample, wherein completion of the disturbing indicates a second dwell start time;
- increasing a second potential difference across the sample at least until a second current flow reaches the threshold value;
- determining a second potential difference value corresponding to the threshold value; and
- determining a second dwell interval, wherein the second dwell interval is a time period between the second dwell start time and a time when the second current flow reaches the threshold value.

19. The computer program of claim 18, where the computer program further comprises executable instructions to cause at least one processor to process a routine for:
- characterizing a relationship between electrical stability of the sample and a plurality of dwell intervals, wherein the characterizing is based at least in part on the first and second dwell intervals and the first and second potential difference values.

20. The computer program of claim 19, where the computer program further comprises executable instructions to cause at least one processor to process a routine for:
- measuring an amount of the first current flow and producing an indication if the amount of the first current flow reaches or exceeds the threshold value.

21. The computer program of claim 20, further comprising executable instructions to cause at least one processor to process a routine for:
- measuring an amount of the second current flow and producing an indication if the amount of the second current flow reaches or exceeds the threshold value.

22. The computer program of claim 17, further comprising executable instructions to cause at least one processor to process a routine for:
- pressurizing the sample to minimize the effects of entrained air bubbles.

23. The computer program of claim 17, further comprising executable instructions to cause at least one processor to process a routine for:
- heating the sample to a test temperature.

* * * * *